(12) United States Patent
Cole et al.

(10) Patent No.: US 12,129,447 B2
(45) Date of Patent: *Oct. 29, 2024

(54) RAPID DISPERSING WET WIPE

(71) Applicant: Rockline Industries, Inc., Sheboygan, WI (US)

(72) Inventors: Douglas B. Cole, Belgium, WI (US); Shankar Krishnamoorthy, Norman, OK (US)

(73) Assignee: Rockline Industries, Inc., Sheboygan, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/236,089

(22) Filed: Aug. 21, 2023

(65) Prior Publication Data
US 2023/0392100 A1 Dec. 7, 2023

Related U.S. Application Data

(63) Continuation of application No. 17/979,196, filed on Nov. 2, 2022, now Pat. No. 12,037,566, which is a continuation of application No. 16/116,142, filed on Aug. 29, 2018, now Pat. No. 11,492,573.

(51) Int. Cl.
| | | |
|---|---|---|
| *C11D 17/04* | (2006.01) | |
| *A61K 8/02* | (2006.01) | |
| *A61K 8/06* | (2006.01) | |
| *A61K 8/34* | (2006.01) | |
| *A61K 8/73* | (2006.01) | |
| *C11D 3/20* | (2006.01) | |
| *C11D 3/22* | (2006.01) | |
| *C11D 3/43* | (2006.01) | |

(52) U.S. Cl.
CPC .......... *C11D 17/041* (2013.01); *A61K 8/0208* (2013.01); *A61K 8/064* (2013.01); *A61K 8/345* (2013.01); *A61K 8/731* (2013.01); *C11D 3/225* (2013.01); *C11D 3/43* (2013.01); *A61K 2800/87* (2013.01)

(58) Field of Classification Search
None
See application file for complete search history.

(56) References Cited

U.S. PATENT DOCUMENTS

| | | | | |
|---|---|---|---|---|
| 5,281,306 A | * | 1/1994 | Kakiuchi | C11D 17/041 |
| | | | | 162/158 |
| 5,798,111 A | * | 8/1998 | Kanga | A61Q 15/00 |
| | | | | 514/937 |
| 6,410,038 B1 | | 6/2002 | Lin et al. | |
| 7,195,771 B1 | | 3/2007 | Hsu et al. | |
| 8,632,636 B1 | | 1/2014 | Tricca et al. | |
| 11,492,573 B2 | * | 11/2022 | Cole | C11D 17/0017 |
| 2003/0017176 A1 | * | 1/2003 | Bleckmann | A61K 8/894 |
| | | | | 514/844 |
| 2004/0076660 A1 | * | 4/2004 | Padlo | A61K 8/0208 |
| | | | | 424/443 |
| 2004/0176263 A1 | * | 9/2004 | Filippini | C09D 9/04 |
| | | | | 510/417 |
| 2006/0275241 A1 | * | 12/2006 | Padlo | A61K 8/9789 |
| | | | | 424/443 |
| 2007/0128137 A1 | * | 6/2007 | Yoshimi | A61K 8/585 |
| | | | | 424/62 |
| 2007/0241306 A1 | | 10/2007 | Wehner et al. | |
| 2007/0274932 A1 | * | 11/2007 | Suginaka | A61K 8/894 |
| | | | | 424/59 |
| 2009/0023620 A1 | | 1/2009 | Ochomogo et al. | |
| 2014/0135406 A1 | | 5/2014 | Lee | |
| 2015/0135457 A1 | | 5/2015 | Dutkiewicz et al. | |
| 2020/0085700 A1 | | 3/2020 | Argo et al. | |
| 2022/0047468 A1 | | 2/2022 | Hurley et al. | |

OTHER PUBLICATIONS

JP 3574318 B2, published on Oct. 6, 2004, with English translation.*
International Search Report and Written opinion dated Dec. 6, 2019 for PCT/US2019/047395.
Supplementary European Search Report and Written Opinion dated May 20, 2021 for EP 19 75 6087.
First Examination Report dated Jun. 1, 2021 for Chilean Patent Application No. 02487-2019.
Office Action dated May 10, 2022 for Mexican Patent Application No. MX/a/2019/010369.
Office Action dated Aug. 21, 2019 for Brazilian Patent Application No. BR112019017866-0.

* cited by examiner

*Primary Examiner* — Lorna M Douyon
(74) *Attorney, Agent, or Firm* — Boyle Fredrickson S.C.

(57) ABSTRACT

A cleaning wipe having a nonwoven substrate impregnated with a dispersal composition including at least one of a polar solvent and a water-in-oil emulsion is disclosed. The dispersal composition provides an enhancement to the dispersion of the nonwoven substrate including a binder when placed within a waste water stream after use, thereby more effectively disposing of the wipe after use.

10 Claims, No Drawings

RAPID DISPERSING WET WIPE

CROSS-REFERENCE TO RELATED INVENTIONS

This application claims priority as a continuation from U.S. Non-Provisional patent application Ser. No. 17/979,196, filed on Nov. 2, 2022, now U.S. Pat. No. 12,037,566, issued on Jul. 16, 2024, which is a continuation from U.S. Non-Provisional patent application Ser. No. 16/116,142, filed on Aug. 29, 2018, now U.S. Pat. No. 11,492,573, issued on Nov. 8, 2022, the entirety of which are each expressly incorporated by reference herein for all purposes.

FIELD OF THE INVENTION

The present invention generally relates to wet wipes and to wet wipes that are rapidly dispersible upon contact with water.

BACKGROUND OF THE INVENTION

An increasing number of consumers are seeking personal care and cleaning products that not only are more natural or sustainable, but which also exhibit better overall performance in use while being environmentally conscious. Consumers prefer products that can be readily used around themselves, children and pets in convenient forms such as pre-loaded disposable wipes or ready to use sprays, but these more sustainable products still are expected to deliver performance on many attributes, such as cleaning and reduction of germs, at parity to traditional products.

In particular, personal care wet wipes, or hard surface cleaning wipes, have gained wide public acceptance. Cleaning wipes include various types of cleaning and disinfecting compositions, as well as waxes and polish to clean furniture and/or other metal, plastic and/or wood surfaces. Wet wipes can further include soaps and/or detergents to clean countertops, floors, appliances, and/or the like. Wet wipes can include surfactants, emollients, fragrances and preservatives for skin contact cleaning. Short chain alcohols and various other biocides can also be included on cleaning wipes to disinfect or sanitize a variety of surfaces.

One aspect in which these traditional wet wipe cleaning systems continue to present challenges is with regard to the ability of the wipes to be disposed of after use in an environmentally friendly manner. Prior art wet wipes attempt to address this issue by utilizing nonwoven materials made from specific fibers and fiber blends in a nonwoven substrate, and/or employing various fiber compositions and formations and/or fiber bonding techniques which require water and turbulence in wastewater systems to disperse the nonwoven substrate into small pieces and subsequently fibers over longer periods of time in contact with mechanical agitation in water or waste water.

However, current wet wipe nonwoven constructions only enable the wipe substrate to be broken down and/or disintegrate when subjected to mechanical agitation in water or wastewater. Current flushability standards (GD3) for nonwoven disposable products requires greater than 25% of the nonwoven dry mass to pass through the sieve after 90 minutes of agitation in water. Further, more stringent flushability standards (GD4) for nonwoven disposable products going into effect in late 2018 requires greater than 60% of the nonwoven dry mass to pass through the sieve after 60 minutes of agitation in water. As such, in view of the present state of the art of wet wipe compositions, there is a need for an improved wet wipe that can be used in a variety of applications related to personal care cleaning, surface cleaning, antibacterial, disinfecting, sanitizing, and/or surfaces without the disposal deficiencies presented above.

SUMMARY OF THE INVENTION

In light of the foregoing, in one exemplary embodiment the invention is directed to an effective wet wipe cleaning system that is formed with a dispersal composition providing increased breakdown, disintegration or dispersal of the wet wipe nonwoven and components thereof when contacted with water upon disposal after use. The rapid dispersing wet wipe nonwoven disperses in less than 60 seconds under the GD4 testing standards. Other components are optionally present in the dispersal composition or any other cleaning composition impregnated within the wet wipe formulation composition to provide the desired cleaning effects, such as, for example, water, surfactants, emollients, solvents, skin conditioning agents, humectants, fragrances, botanical extracts, oils, silicones, preservatives and the like, and combinations of the same. All components of the formulation are blended together to form a wet wipe formula composition which includes, solution or emulsion that can be impregnated within or otherwise applied to a nonwoven, cloth or paper substrate, or combinations of the same to form a usable wet wipe for storage and consumer use.

In one exemplary embodiment, the wet wipe formula composition includes a dispersal composition having a polar solvent that works in conjunction with a dispersable substrate material to increase the speed of dispersal or disintegration of the wet wipe nonwoven substrate. The dispersal composition and solvent maintains a suitable strength of the nonwoven substrate material when packaged, in storage and during use, but rapidly disperses or disintegrates the nonwoven substrate material into smaller pieces and fibers when contacted with water in toilets, septic and waste water systems. In an exemplary embodiment the solvent in the dispersal composition is a diol and/or a polyhydric alcohol.

According to another exemplary embodiment of the invention, the wet wipe composition includes a dispersal composition providing increased speed of dissolution of the wet wipe nonwoven substrate where the dispersal composition includes a water-in-oil emulsion. The water-in-oil emulsion maintains a suitable strength of the substrate material when packaged, in storage and during use, but rapidly disperses the substrate material when contacted with water in toilets, septic and waste water systems.

According to another exemplary embodiment of the invention, the wet wipe composition includes a dispersal composition for increasing the speed of dispersal of the wet wipe including each of a solvent, e.g., a diol and/or a polyhydric alcohol, and a water-in-oil emulsion.

Other features, benefits and advantages of the present invention will be apparent from this summary and its descriptions of certain embodiments of such formulations and compositions, and will be readily apparent to those skilled in the art having knowledge of the synthetic techniques described therewith. Such features, benefits and advantages will be apparent from the above as taken into conjunction with the accompanying examples, data, and all reasonable inferences to be drawn therefrom.

DETAILED DESCRIPTION OF CERTAIN EMBODIMENTS

The invention relates to a formulation for a wet wipe composition comprising a substrate material and a dispersal composition contained on and/or within the substrate material including at least one of a solvent and a water-in-oil emulsion that provides enhanced dispersal of the substrate material upon contact with waste water systems after use of the wet wipe. The wet wipe composition of the invention can be used, for example, on wet wipes for flushable wet wipes, flushable moist wipes, flushable personal wipes, and flushable toilet cleaning wipes, among others. As used herein, a "wipe" is a type of article suitable for cleansing or disinfecting or for applying a compound and/or removing materials and compounds from surfaces, such as those disclosed in U.S. Pat. Nos. 7,101,612; 6,814,974; and 6,444,214, each of which is hereby expressly incorporated by reference in its entirety for all purposes. In particular, this term refers to an article for cleansing a hard surface, including the removal of waste or other undesired material from the hard surface.

According to one exemplary embodiment of the invention, the wet wipe is formed of a non-woven material, onto or into which the dispersal formula composition and other suitable cleaning compositions are impregnated. The nonwoven material can be any suitable composition capable of interacting with the dispersal composition to produce rapid dispersal of the wet wipe in water. In one exemplary embodiment of the present invention, the substrate material is an absorbent substrate is preferably water-insoluble. By "water-insoluble" is meant that the substrate does not dissolve but may readily break apart into smaller pieces or components upon immersion in water. The water-insoluble substrate is the implement or vehicle for delivering the cleaning composition of the present invention to the surface being cleaned, disinfected or sanitized. As used herein, the terms "substrate" or "wipe" are intended to include any material on which a composition may be loaded or impregnated with a formulation. In functional applications, a nonwoven substrate is used to clean an article or a surface, as by wiping. Substrates comprise woven or nonwoven materials, typically made from a plurality of fibers. The substrate can be used by itself (typically by hand) or attached to a cleaning implement, such as a floor mop, handle, or a handheld cleaning tool, such as a toilet cleaning device. A wide variety of materials can be used as the substrate. Non-limiting examples of suitable water insoluble substrates include nonwoven substrates, woven substrates, sponges, cloths, meshes, paper towels, napkins, cleaning pads, and the like.

Other exemplary embodiments employ nonwoven substrates since they are economical and readily available in a variety of materials. By nonwoven is meant that the layer is comprised of fibers which are not woven into a fabric but rather are formed into a membrane, sheet, substrate, mat, absorbent core or pad layer or combinations thereof. Nonwoven substrates may be comprised of a variety of materials both natural and synthetic. By natural is meant that the materials are derived from plants, animals, insects or byproducts of plants, animals, and insects. By synthetic is meant that the materials are obtained primarily from various man-made materials or from natural materials which have been further altered. The conventional base starting material is usually a fibrous web comprising any of the common synthetic or natural textile length fibers, or mixtures thereof. Non-limiting examples of natural materials useful in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof. Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof. Examples of some of these synthetic materials include acrylics such as acrilan, creslan, and the acrylonitrile-based fiber, orlon; cellulose ester fibers such as cellulose acetate, arnel, and acele; polyamides such as nylons; polyesters such as fortrel, kodel, and the polyethylene terephthalate fiber, dacron; polyolefins such as polypropylene, polyethylene; polyvinyl acetate fibers; polyurethane foams and mixtures thereof. In one particular example, the substrate is a 65 gsm airlaid nonwoven material from GP.

In one particular exemplary embodiment, the substrate includes pulp fibers, such as bleach softwood kraft fibers with an average length of 2.5 mm, that are coated with a fiber binder system that works in conjunction with the formula to provide rapid dispersion or disintegration of the nonwoven material. The binder acts to maintain the cohesion of the pulp fibers forming the nonwoven wipe substrate and in an exemplary embodiment, the binder is formed of carboxymethylcellulose (CMC), polyvinyl alcohol, polyvinyl acetate or combinations thereof, and one or more divalent salts, such as $CaCl$, and $MgCl$, among others. The binder including these components, such as that disclosed in U.S. Pat. No. 9,439,549, entitled Dispersible Nonwoven Wipe Material, incorporated herein by reference in its entirety for all purposes, acts on the fibers of the substrate to adhere the fibers to one another in order to enable the substrate formed of the fibers to hold the wipe together when impregnated with a cleaning formulation or solution or other composition or other components, as well as during use of the wet wipe. Once contacted with a toilet water or waste water stream, such as when the wipe is flushed after use, the contact of the water with the binder system and dispersal composition combination breaks down the binder to allow the fibers to disassociate and to disperse the wipe nonwoven substrate. The contact time of the wipe in toilet water or waste water to achieve the disassociation and/or dispersal of the fibers to meet the GD4 standards is less than 60 seconds. The binders used in the dispersible nonwoven and the formula are not affected by wastewater components such as water hardness, temperature or dissolved solids.

To enhance the dispersal of the pulp fibers upon contact with the waste water stream after use, the wipe composition additionally includes a dispersal composition impregnated into the wipe substrate. The dispersal composition interacts with the binder to more rapidly break down the binder and cause the disassociation of the fibers forming the wipe substrate. The dispersal composition increases the dispersal of the wipe substrate fibers from those of current and prior art nonwoven disposable products. Current flushability standards (GD3) for nonwoven disposable products require greater than 25% of the nonwoven dry mass to pass through the sieve after 90 minutes of agitation in water. Most commercial flushable wipes require greater than 20 minutes for wipes dispersion. This nonwoven wipe with the dispersal composition of the present disclosure decreases wipe dispersion time to less than 60 seconds under the same conditions. While not wishing to be bound by any particular theory, it is believed that specific components in both the substrate material and binder formulation are diluted in toilet water or waste water causing ingredient dilution and shift in component polarity causing the strength of the binder system to lose integrity. When the dispersal composition is impregnated onto the dispersible nonwoven material, the dispersal composition provides and maintains suitable strength of the nonwoven in package, storage and during use, but rapidly counteracts the effects of the binder and disperses the nonwoven into fibers when contacted with toilet water or wastewater systems.

In one exemplary embodiment, the dispersal composition includes, and optionally is exclusively formed with, a polar solvent that interacts with the binder to improve the disassociation of the fibers of the wipe substrate material. The solvent, in one exemplary and non-limiting embodiment is a diol and in certain exemplary embodiments the solvent is selected from $C_3$-$C_{10}$ diols, including a 1,3 diol, such as 2-methyl-1,3-propanediol, which has the following structure:

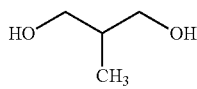

The solvent in another exemplary and non-limiting embodiment is a polyhydric alcohol that can be used alone or in combination with the diol and in certain exemplary embodiments the solvent is selected from $C_4$-$C_6$ polyhydric alcohols, including a hexahydric alcohol such as sorbitol or mannitol which have the following structures:

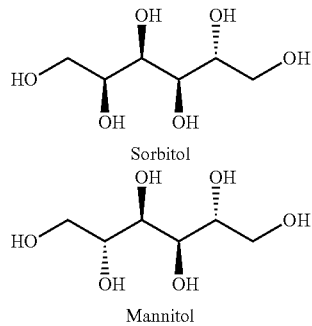

In one embodiment, the polar solvent is not propylene glycol, as propylene glycol used as the solvent has the effect of not maintaining or providing sufficient wet wipe strength and integrity in package, use and storage when employed in the dispersal composition or formulation. In another exemplary embodiment, the polar solvent in the dispersal composition is 1,3-propanediol which has a different molecular polarity from propylene glycol (1,2-propanediol) and interacts with the binder composition to create a rapid dispersing wet wipe in water while maintaining suitable wipe strength in package, use and storage. Little to no agitation is required for complete disassociation/dispersion of the dispersible nonwoven when impregnated with the dispersal composition including the 1,3-propanediol after depositing in toilet water or wastewater systems. To assess the ability of the dispersal composition to enable the disassociation of the nonwoven fibers, a nonwoven wipe formed with the dispersal composition/formulation was tested in a slosh box disintegration test unit as described in the Guidelines for Assessing the Flushability of Disposable Nonwoven Products, 3rd Ed., which is expressly incorporated herein by reference in its entirety for all purposes. The results showed that a nonwoven wipe with the dispersal composition of the present disclosure decreases wipe dispersion time to less than 60 seconds under these test conditions. In certain exemplary embodiments, the dispersal composition is formed as an aqueous solution where the solvent, such as 1,3-propanediol, level is at least 25% w/w, more preferably at least 30% w/w and even more preferably at least 35% w/w of the dispersal composition or formulation. The dispersal composition, along with other components in an impregnated cleaning and binder formula such as water, surfactants, emollients, fragrances, extracts, oils, silicones and combinations of some or all components, are blended together to form a wet wipe solution that can be applied to the above dispersible nonwoven material to form a rapid dispersing wet wipe suitable for consumer use.

In another exemplary embodiment, the dispersal composition can be formed with, and optionally exclusively with, a water-in-oil emulsion that interacts with the binder to improve the disassociation of the fibers of the wipe substrate material. Additionally, the dispersal composition is not formed as an oil-in-water emulsion as oil-in-water emulsions have been determined not to maintain or provide sufficient wet wipe strength and integrity in package, use and storage, nor can dispersal formulation formed with oil-in-water emulsions function as a dispersal enhancing composition in the manner of a water-in-oil emulsion and thus are unsuitable for use as the dispersal composition. The water-in-oil emulsion is impregnated onto the above mentioned dispersible nonwoven material, provides and maintains suitable strength of the nonwoven in packaging, storage within the packaging and during use, but rapidly disperses into fibers when contacted with toilet water or wastewater systems. Similarly to the embodiment where the dispersal composition is formed of the 1,3-propanediol and/or polyhydric alcohol, this embodiment for the dispersal composition requires little to no agitation for dispersion of the above mentioned dispersible nonwoven after depositing in toilet water or wastewater systems as determined in slosh box disintegration testing as described previously. In certain exemplary embodiments the water-in-oil dispersal composition is formed, optionally exclusively, as an emulsion where the external emulsion oil phase is at least 25% w/w, more preferably at least 30% w/w and even more preferably at least 40% w/w of the weight percent of the dispersal formulation. The oil can be selected from mineral oil, silicones, long chain esters, long chain ethers, long chain alkanes and combinations of some or all of these oils, among others. The above disclosed ingredients, along with other components in a formula such as water, emulsifiers, emollients, fragrances, extracts, oils, silicones and combinations of some or all components, are blended together to form a wet wipe emulsion that can be applied to the dispersible nonwoven material to form a rapid dispersing wet wipe suitable for consumer use.

In other exemplary embodiments, the dispersal composition or formulation can be formed from, and optionally exclusively from, a combination of the polar solvent, e.g., 1,3-propanediol and/or the polyhydric alcohol, and the water-in-oil emulsion. In this exemplary embodiment of the dispersal composition, the internal water phase of the water-in-oil emulsion contains at least 20% w/w of the 1,3 propanediol and/or polyhydric alcohol, more preferably at least 25% w/w and even more preferably at least 30% w/w of the of emulsion dispersal composition with balance consisting of water is formed. The level of the 1,3 propanediol and/or polyhydric alcohol in the internal water phase is the weight percent of the formulation. As stated above, the wet wipes including the dispersal composition and/or the dispersal composition itself may optionally include and/or be used in combination with one or more additional components or adjuncts. The adjuncts include, but are not limited to, water, surfactants, emollients, fragrances and/or perfumes, botanical extracts, oils and/or lotions, silicones, waxes, dyes and/or colorants, solubilizing materials, stabilizers, thickeners, defoamers, hydrotropes, chelating agents, buffers, builders, enzymes, solvents, bleaching agents, cloud point modifiers, preservatives and/or combinations of the same.

Example 1—The following are the components and amounts of the same that represent a specific working example of the wet wipe and dispersal composition provided herein (percentages are by weight in finished product).

1) Nonwoven material 75% by wt of the wipe
   Dispersal composition 25% by wt of the wipe Example 2—Table 1 represents a specific example of a dispersal composition according to the invention that can be loaded onto a cleaning wipe.

| Ingredient | % in dispersal Composition | % active/purity | % in final Product (on wipe) |
|---|---|---|---|
| Water | 62.70 | 100.00 | 90.675 |
| 1,3 Propanediol | 35.00 | 100.00 | 8.75 |
| PEG-8 Dimethicone | 1.00 | 100.00 | 0.25 |
| Hydroxyacetophenone | 0.50 | 100.00 | 0.125 |
| Sodium Benzoate | 0.30 | 100.00 | 0.075 |
| Citric Acid | 0.25 | 100.00 | 0.0625 |
| Fragrance | 0.25 | 100.00 | 0.0625 |

It is noted that the range of the dispersal solution impregnated into the substrate includes from between 100% to 500% w/w of the dry weight of the substrate.

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

What is claimed is:

1. A cleaning wipe comprising:
   a) a substrate formed from fibers coated with a binder composition, the binder composition consisting of:
      i) a component selected from the group consisting of: polyvinyl alcohol, polyvinyl acetate, and combinations thereof; and
      ii) a divalent salt; and
   b) a dispersal composition loaded onto the substrate, the dispersal composition comprising a water-in-oil emulsion including a polar solvent in the emulsion, wherein the polar solvent is selected from the group consisting of a diol, a polyhydric alcohol, and combinations thereof, wherein the polar solvent does not include propylene glycol, wherein the polar solvent is present in an amount of at least 25% w/w of the dispersal composition, and
   wherein an external oil phase of the emulsion is at least 30% w/w of the dispersal composition.

2. A cleaning wipe according to claim 1, wherein the polar solvent is present in an amount of at least 30% w/w of the dispersal composition.

3. A cleaning wipe according to claim 1, wherein the polar solvent is a $C_3$-$C_{10}$ diol.

4. A cleaning wipe according to claim 1, wherein the polar solvent is 1,3 diol.

5. A cleaning wipe according to claim 1, wherein the polar solvent is 1,3-propanediol.

6. A cleaning wipe according to claim 1, wherein the polar solvent is sorbitol.

7. A cleaning wipe according to claim 1, wherein the water-in-oil emulsion comprises the polar solvent in a water phase of the water-in-oil phase of the emulsion.

8. A cleaning wipe according to claim 1, wherein the water-in-oil emulsion comprises at least 25% w/w of the dispersal composition.

9. A method of cleaning a surface, the method comprising the steps of:
   a) providing a cleaning wipe according to claim 1;
   b) applying the cleaning wipe to the surface; and
   c) placing the cleaning wipe within a waste water stream to disperse the cleaning wipe.

10. A method according to claim 9, wherein the step of applying the cleaning wipe to the surface comprises applying the cleaning wipe to a personal care surface.

* * * * *